US00PP20615P3

(12) United States Plant Patent

Rood et al.

(10) Patent No.: US PP20,615 P3

(45) Date of Patent: Dec. 29, 2009

(54) OAK TREE NAMED 'ADELINE'

(50) Latin Name: *Quercus bicolor×Quercus robur*
Varietal Denomination: Adeline

(75) Inventors: Michael Anthony Rood, Herman, MO (US); William Walkenbach, Herman, MO (US)

(73) Assignee: Michael A. Rood, Hermann, MO (US)

( * ) Notice: Subject to any disclaimer, the term of this patent is extended or adjusted under 35 U.S.C. 154(b) by 0 days.

(21) Appl. No.: 12/005,634

(22) Filed: Dec. 28, 2007

(65) Prior Publication Data

US 2009/0172848 P1 Jul. 2, 2009

(51) Int. Cl.
*A01H 5/00* (2006.01)

(52) U.S. Cl. ..... Plt./225

(58) Field of Classification Search ..... Plt./225
See application file for complete search history.

*Primary Examiner*—Annette H Para
*Assistant Examiner*—Louanne C Krawczewicz Myers

(57) ABSTRACT

A new and distinct Hybrid Oak tree named 'Adeline' characterized by its very narrow pyramidal habit of growth, its winter hardiness, and hybrid vigor. Also for its dark green, mildew-resistant foliage and its ability to withstand wind and ice without breakage.

6 Drawing Sheets

The present invention comprises a new and distinct cultivar of a $F_1$ hybrid oak tree, botanically known as *Quercus bicolor×Quercus robur* 'Fastigiata' also botanically known as the Ware oak *Quercus×warei* and referred to by the cultivar name 'Adeline'. The seed parent *Quercus bicolor* is an unnamed and unpatented plant and the pollen parent *Quercus robur* 'Fastigiata' is unpatented. The 'Adeline' oak tree is growing in a cultivated area at the home of William Walkenbach, 1820 Hwy. West, Hermann, Mo. 65041, in Gasconade County, Township 45 North, Range 5 West, Section 16.

The 'Adeline' cultivar is an extremely narrow-upright pyramidal form (FIG. 1) that keeps a narrow pyramidal form from its base to its top. It is very strong wooded tree with dark green leathery foliage (FIG. 4) that is highly resistant to powdery mildew. Its parentage would indicate it to be hardy in Zone 4b and possibly 4a, (U.S.D.A. Hardiness Zone Map). The new 'Adeline' cultivar has been successfully asexually propagated by chip budding onto unnamed and unpatented *Quercus bicolor* seedling rootstocks. The asexual reproduction occurred at 846 Hoagland Rd. Jacksonville, Ill. 62650. Bud take has been near 95% with no incompatibility between the scion and rootstock.

Buds set on two year rootstocks have produced five to six feet (152.4–182.9 cm) of growth in one growing season. Asexually propagated trees of the 'Adeline' cultivar have maintained their unique characteristics which, in combination, distinguish this cultivar selection from both of its parents, *Quercus bicolor* and *Quercus robur* 'Fastigiata' (FIG. 3).

1. The 'Adeline' oak tree at 15 years of age is 25 feet (7.6m) in height, with a total limb spread of seven feet (2.1 m). The narrow form of the 'Adeline' oak tree could be used in several different ways in the landscape. It can be planted on city streets where a very limited space exists. It could also be planted to form a narrow screen or windbreak. It would lend itself well in a landscape planting where repetition of a narrow pyramidal form would be desired or it could be planted in a park or on a golf course as a specimen tree.

2. The 'Adeline' oak is highly resistant to wind and ice. It has never suffered any breakage from either wind or ice. Its pistillate parent, *Quercus bicolor*, would account for the resilience of its wood during storms. The species *Quercus bicolor* is known for having wood of great strength.
3. Foliage of the 'Adeline' hybrid oak tree is dark green on the upper surface and silvery light green on the undersurface (FIG. 4). This tree has also proven to be highly resistant to powdery mildew.
4. Compared to *Quercus robur* 'Fastigiata', this new hybrid is far more winter hardy.
5. The 'Adeline' oak exhibits remarkable hybrid vigor. A chip bud set on a two-year old *Quercus bicolor* seedling will make five to six feet of growth in one growing season.

DETAILED BOTANICAL DESCRIPTION

In the following description, color references are made to The Royal Horticultural Society Colour Chart published in 1966.

BRIEF DESCRIPTION OF THE DRAWINGS

The accompanying colored photographs illustrate the appearance and color of the new oak tree. These photographs show the color as accurately as is reasonably possible to obtain in colored reproductions of this type. Actual foliage colors may differ slightly due to light reflectance.

THE PLANT

TREE, HYBRID OAK 'Adeline'

Name: Cultivar 'Adeline'

Figure 1:
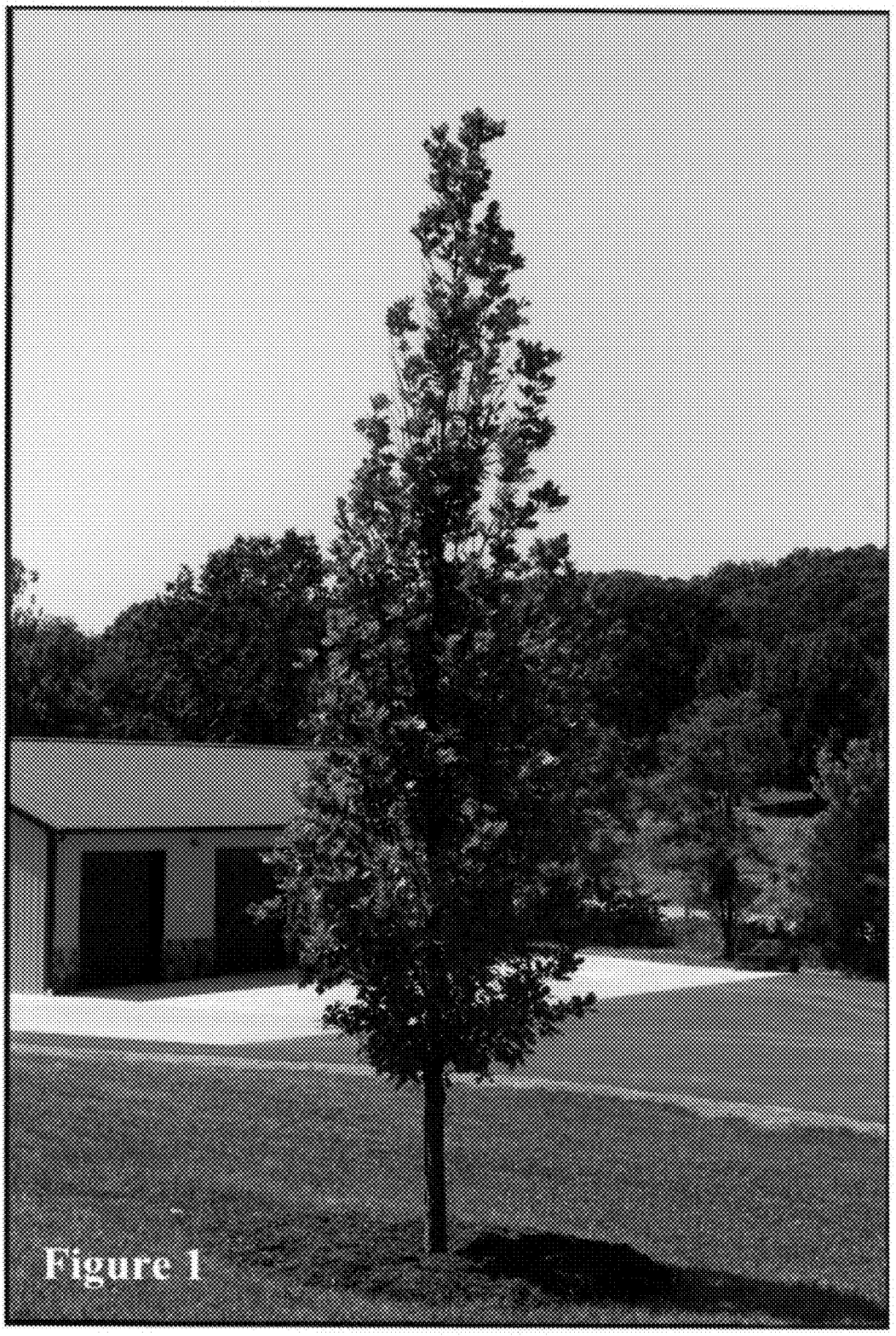
FIG. 1 depicts the initially discovered tree named in summer foliage showing its very narrow form.
Figure 2:
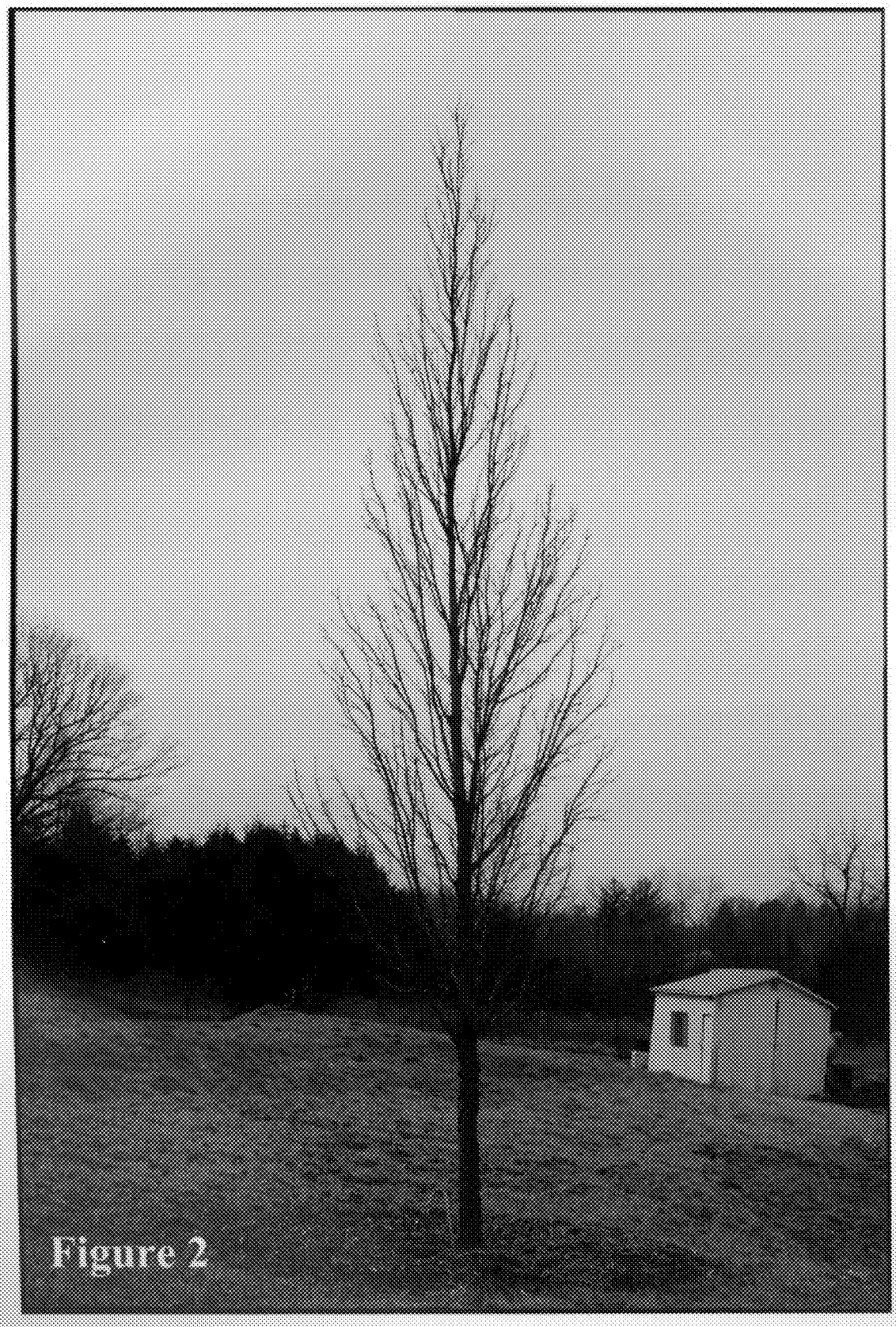
FIG. 2 depicts the oak tree without foliage.
Figure 3:
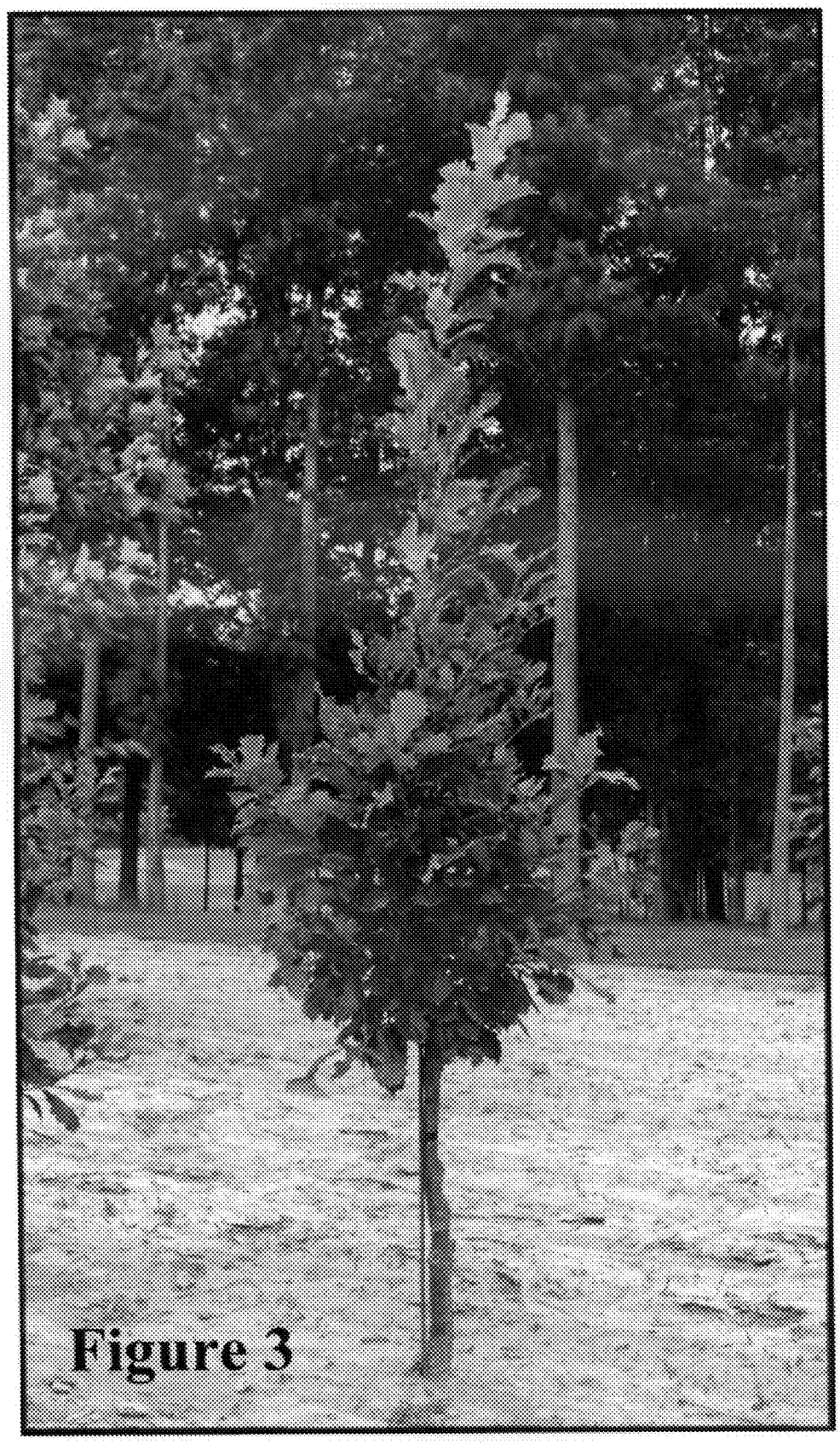
FIG. 3 depicts the first asexually propagated (chip budded) tree of the cultivar.
Figure 4:
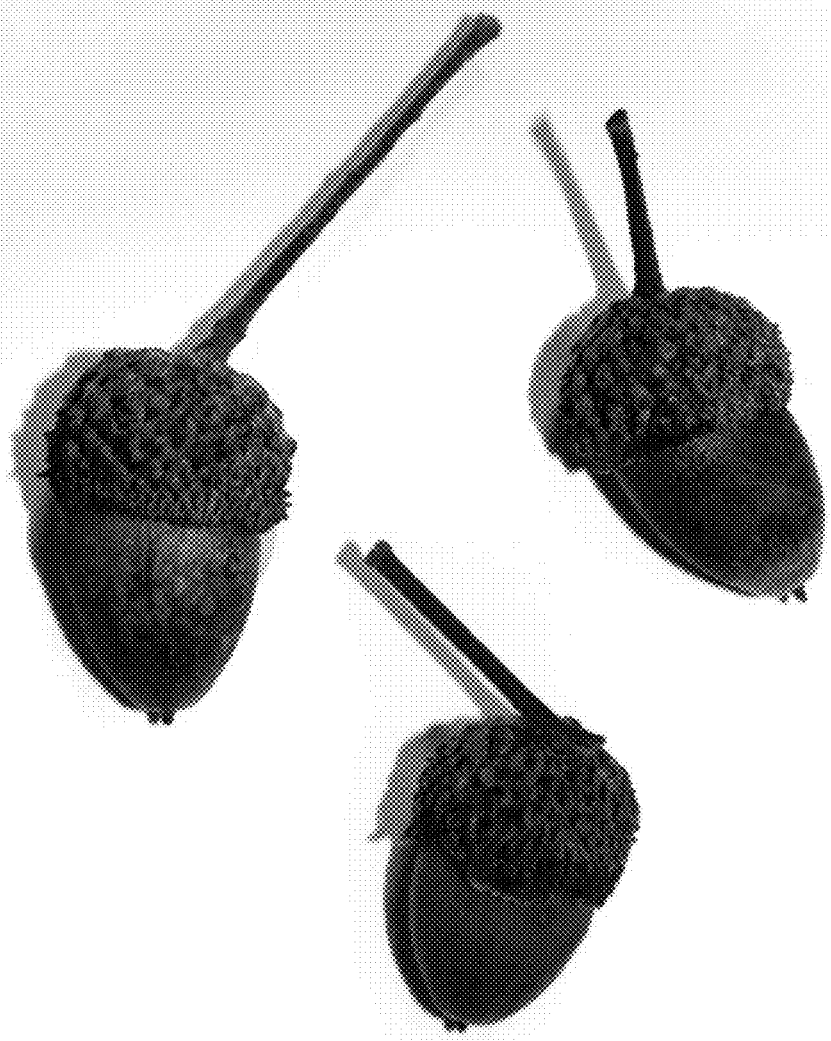
FIG. 4 depicts the mature acorn and peduncle of the oak in late autumn.
Figure 5:
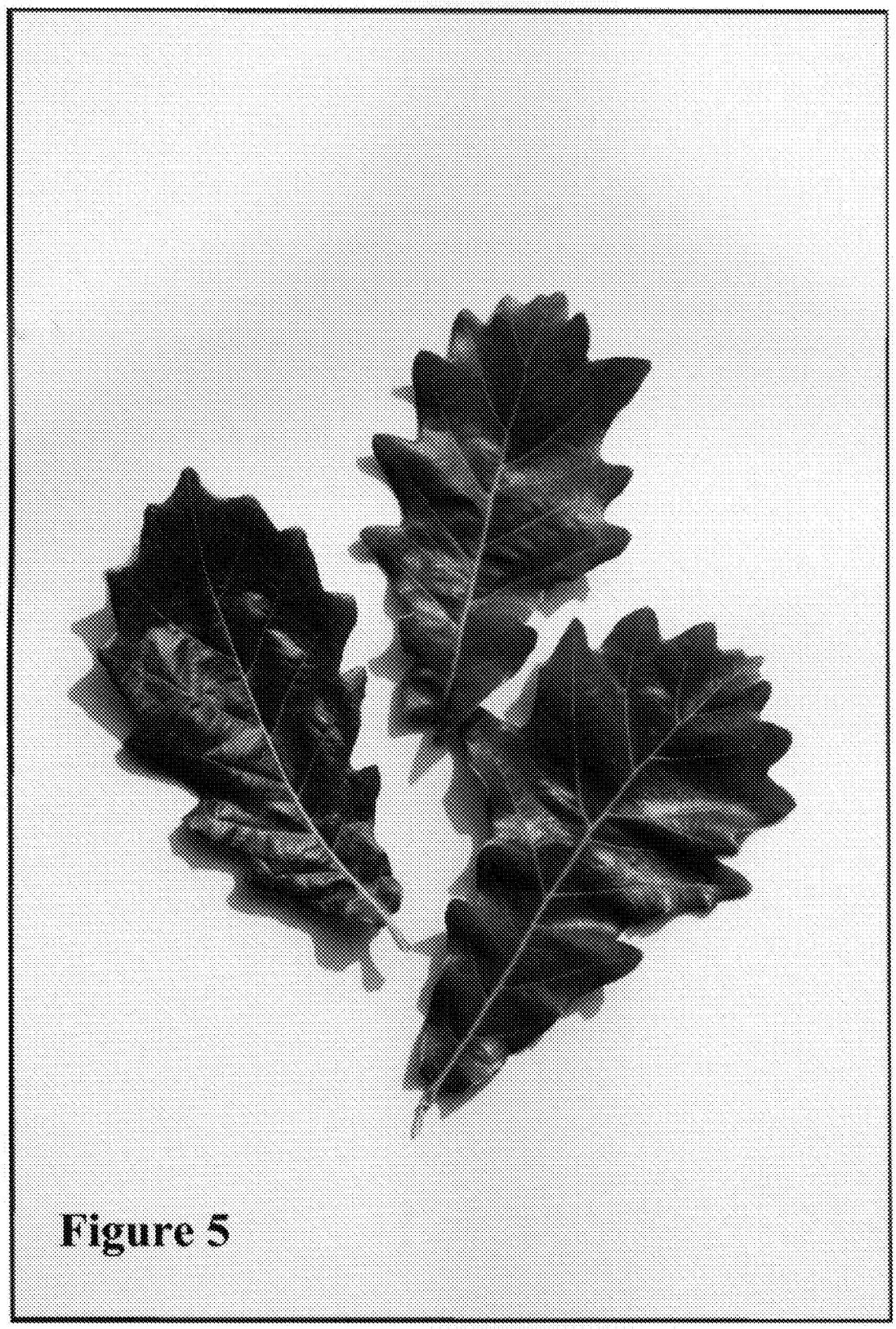
FIG. 5 depicts the foliage of the 'Adeline' cultivar, upper surface of the leaf shows no evidence of powdery mildew.
Figure 6:
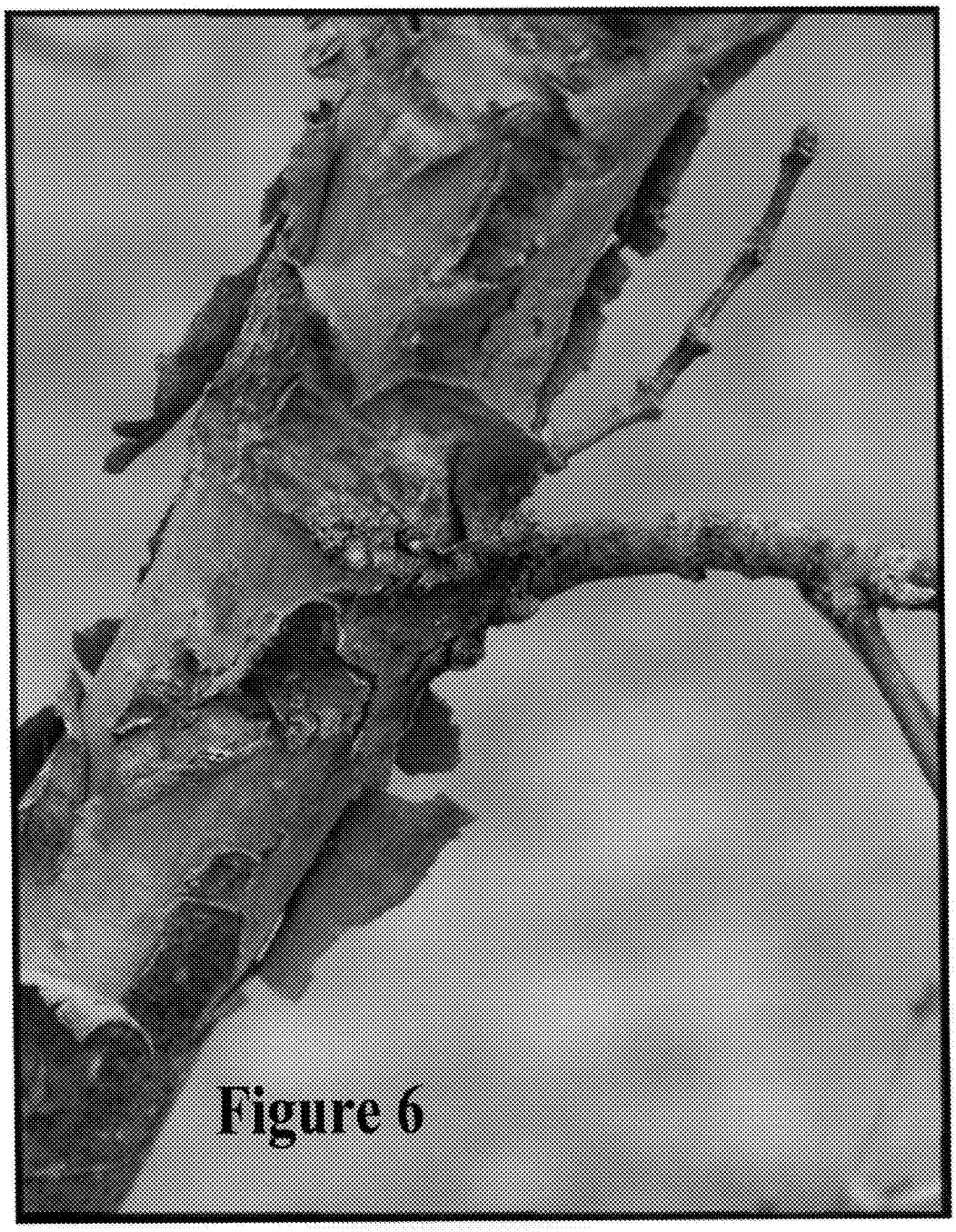
FIG. 6 depicts the stem, including terminal and lateral buds.

Parentage: Seedling, 1991 Seed parent *Quercus bicolor* Pollen parent *Quercus robur* 'Fastigiata'

*Botanic name.*—*Quercus bicolor*×*Quercus robur* 'Fastigiata', hybrid oak as known as *Quercus*×*warei.*

*Discovered.*—In a cultivated area, at the home of William Walkenbach, 1820 Hwy. West, Hermann, Mo. 65041, Gasconade County, Township 45 North, Range 5 West, Section 16. This plant has been asexually reproduced by grafting (chip budding) onto Swamp White Oak *Quercus bicolor* seedling rootstock. Presently, propagation is being performed at three different nurseries with one nursery in each of the following states Illinois, Missouri, and Oregon.

*Form.*—Tree.

*Shape.*—Narrow pyramidal.

*Height.*—7.62 m (25'); Spread 2.13 m (7').

*Trunk size* (*diameter of trunk at* 137 *cm above ground level*).—9.53 cm (3.75").

*Base.*—Cylindrical.

*Growth rate.*—Excellent, with robust hybrid vigor.

*Strength.*—Excellent.

*Age.*—15 years from a planted acorn.

*Bark* (*Trunk*).—Bark dark grey to light grey (197A&B); small rectangular blocks with vertical furrows; medium-course in texture, size of blocks are 1.9–2.54 cm (0.75–1.0") wide, 3.81–6.35 cm (1.5–2.5") long.

Branches:

*Angle of attachment.*—Lower branches between 30° and 60° with the upper portion of the tree at 20° to 30°.

*Spacing.*—Dense. Small Twig Bark: (<0.7 cm diameter) (growing season) greenish, smooth (195A) (dormant season) grey-green (197A) and grey-purple(183A).

*Lenticels.*—Small (μ=0.4 mm) on branches less than 6 mm in diameter, scattered, round, raised, color (196C).

*Small branch bark.*—(0.7–2.5 cm diameter) gray (198A) mottled with brown (199B), smooth, exfoliation begins at 1.3 cm in diameter.

Leaves:

*Petiole.*—Length: (0.3–1.0 cm, μ=0.59 cm) Color: green (144B&C) Texture: smooth.

*Lamina.*—Length: 5.08–14.9 cm, (μ=11.6 cm) Width: 3.0–8.6 cm, (μ=6.6 cm) Form: Lamina: obovate; base cuneate to acute narrowly cordate on some leaves; apex obtuse to broadly acute. Margin: shallowly lobed with 6–8 pairs of obtuse teeth. Texture: Membranous, leathery, glossy, smooth, glabrous above, and pubescent on underside. Quantity: abundant. Color: Upper side: (summer) dark green (139A) (autumnal) color changes from shades of yellow-green (152A, 153A, & 154A) to brown (199A). Lower side: leaves are grayish green (193A). Ribs and Veins: 6–8 pairs of lobes with 10–12 pairs of veins; greenish-yellow (151B); pinnate pattern of venation.

Buds: (Vegetative) Small triangular in shape (0.16–0.5 cm) μ=0.3 cm, gray-orange, (176A) and brown (199D) covered with an imbricate pattern of scales Flowers: Imperfect, monoecious; staminate aments are pendent, clustered, length cm (μ=6.0 cm) color of aments, yellow-green (150A) to yellow-green (150C); pistillate flowers found in axils of emerging new leaves, ovary surrounded by a calyx which is enclosed in a cupule, 0.8 mm in length, yellow-green in color (150C)

Fruit: On peduncle (1.3–4.6 cm), μ=2.5 cm long, mostly solitary or with undeveloped second fruit; cap gray-brown (199D) with warty scales; cap measures (1.8–2.5) cm with μ=2.4 cm wide by (1.3–1.8) cm with (μ=1.4 cm) long; nut gray-orange 166 A, 165 A and B ( 2.3–2.8 ) cm, μ=2.5 cm long by (1.4–2.0) cm, 9μ=1.7 cm) wide, apex sharp point (0.6–1.6 mm), (μ=1.2 mm) long; ovoid; cap encloses nut (40–60%), μ=50%.

HAS THIS PLANT EVER BEEN OFFERED FOR SALE? No

Compare this new variety with others of the same species and with its parent or parents; state the distinguishing characteristics of the new cultivar and its advantages.

This tree is an extremely narrow-pyramidal form. It is similar to the oak cultivars 'Nadler' U.S. Plant Pat. No. 17,604 and 'Long' U.S. Plant Pat. No. 12,673 in leaf appearance, bark character, and fruit size, but differs in having a very narrow pyramidal shape in contrast to the narrow columnar form of the Nadler oak and the medium-oval form of the 'Long' oak. Swamp white oak (*Quercus bicolor*) the seed parent of the 'Adeline' oak tree develops a broad open round-topped crown and a short trunk in contrast to the narrow-pyramidal form of the 'Adeline' cultivar. The 'Adeline' oak differs from the form of its pollen parent, *Quercus robur* 'Fastigiata', by having a very narrow-pyramidal form instead of a fastigiate habit of growth. It also differs from *Quercus robur* 'Fastigiata' by having mildew-resistant dark, shiny green leaves with a silvery-white underside. It has bold, dark green, mildew-resistant foliage with highly ornamental silvery lower surfaces similar to its seed parent. This tree's genetic heritage has made it winter hardy, adaptable to almost any soil, and tolerant of drought and flooding.

It is claimed:

1. A new and distinct cultivar of hybrid oak tree *Quercus bicolor*×*Quercus robur* 'Fastigiata', named 'Adeline', as illustrated and described.

* * * * *